(12) United States Patent
Foster et al.

(10) Patent No.: US 9,718,036 B2
(45) Date of Patent: Aug. 1, 2017

(54) METHOD OF PREPARING CARRIER LIQUIDS

(75) Inventors: Alison Jayne Foster, Liverpool (GB); James Long, Liverpool (GB); Steven Paul Rannard, Liverpool (GB); Dong Wang, Liverpool (GB)

(73) Assignee: The University of Liverpool, Liverpool (GB)

(*) Notice: Subject to any disclaimer, the term of this patent is extended or adjusted under 35 U.S.C. 154(b) by 400 days.

(21) Appl. No.: 14/241,965

(22) PCT Filed: Aug. 20, 2012

(86) PCT No.: PCT/GB2012/052028
§ 371 (c)(1),
(2), (4) Date: Feb. 28, 2014

(87) PCT Pub. No.: WO2013/030535
PCT Pub. Date: Mar. 7, 2013

(65) Prior Publication Data
US 2014/0212466 A1    Jul. 31, 2014

(30) Foreign Application Priority Data

Aug. 31, 2011 (GB) .................................. 1115079.4

(51) Int. Cl.
| | | |
|---|---|---|
| *B01F 3/20* | (2006.01) | |
| *A61K 9/14* | (2006.01) | |
| *A61Q 15/00* | (2006.01) | |
| *A01N 31/12* | (2006.01) | |
| *A01N 47/38* | (2006.01) | |
| *A01N 53/00* | (2006.01) | |
| *A61Q 19/00* | (2006.01) | |
| *A61K 8/04* | (2006.01) | |
| *A61K 9/19* | (2006.01) | |
| *A01N 25/04* | (2006.01) | |
| *A61K 9/10* | (2006.01) | |
| *A23L 27/00* | (2016.01) | |
| *A23L 27/30* | (2016.01) | |
| *B82Y 40/00* | (2011.01) | |

(52) U.S. Cl.
CPC ............ *B01F 3/2064* (2013.01); *A01N 25/04* (2013.01); *A01N 31/12* (2013.01); *A01N 47/38* (2013.01); *A01N 53/00* (2013.01); *A23L 27/30* (2016.08); *A23L 27/82* (2016.08); *A61K 8/04* (2013.01); *A61K 9/10* (2013.01); *A61K 9/145* (2013.01); *A61K 9/146* (2013.01); *A61K 9/19* (2013.01); *A61Q 19/00* (2013.01); *A61K 2800/10* (2013.01); *A61K 2800/412* (2013.01); *A61K 2800/413* (2013.01); *A61K 2800/84* (2013.01); *B82Y 40/00* (2013.01)

(58) Field of Classification Search
None
See application file for complete search history.

(56) References Cited

U.S. PATENT DOCUMENTS 5,589,194 A * 12/1996 Tsuei ................... A61K 9/1617
   252/301.6 S
6,862,890 B2 *  3/2005 Williams, III ....... A61K 9/1617
   264/13

FOREIGN PATENT DOCUMENTS

| WO | 2004/011537 | 2/2004 |
| WO | 2006/079410 | 8/2006 |
| WO | 2008/007150 | 1/2008 |
| WO | 2012/045994 | 4/2012 |

OTHER PUBLICATIONS

Yassin, A. E., et al. "Optimization of 5-fluorouracil solid-lipid nanoparticles: a preliminary study to treat colon cancer." Int J Med Sci 7.6 (2010): 398-408.*
Singh, Sanjay, et al. "Formulation and evaluation of solid lipid nanoparticles of a water soluble drug: zidovudine." Chemical and pharmaceutical bulletin 58.5 (2010): 650-655.*
International Search Report for Application No. PCT/GB2012/052028 dated Mar. 13, 2013 (3 pages).
Zhang, H. et al, "Formation and enhanced biocidal activity of water-dispersable organic nanoparticles," Nature Nanotechnology, vol. 3, Aug. 2008, pp. 506-511 (6 pages).

* cited by examiner

*Primary Examiner* — Nissa Westerberg
(74) *Attorney, Agent, or Firm* — Michael Best & Friedrich LLP

(57) ABSTRACT

The invention provides a method for the preparation of a carrier liquid which comprises the steps of: (I) preparing a single phase solution comprising: (a) a solvent or a mixture of miscible solvents, (b) a liquid carrier material, which is soluble in solvent (a), and (c) a dopant material which is also soluble in solvent (a); (II) cooling (preferably freezing) the single phase solution produced in step (I) to a temperature at which at least both the solvent (a) and carrier material (b) become solid; and (III) removing solid solvent (a) from the cooled (frozen) single phase solution in vapor form, such that the remaining cooled (frozen) carrier material (b) and dopant material (c) are returned to ambient temperature thus providing a product of liquid carrier material (b) having dopant material (c) dispersed therein.

17 Claims, No Drawings

METHOD OF PREPARING CARRIER LIQUIDS

CROSS-REFERENCE TO RELATED APPLICATIONS

This patent application is a national stage filing under 35 U.S.C. §371 of International Application No. PCT/GB2012/052028, filed on Aug. 20, 2012, which claims the benefit of priority to Great Britain Patent Application No. 1115079.4, filed on Aug. 31, 2011, the disclosures of which are incorporated by reference herein in their entireties.

FIELD OF THE INVENTION

The present invention relates to carrier liquids and to methods of producing such liquids.

BACKGROUND

WO2004/011537 describes the formation of solid, porous beads comprising a three-dimensional, open-cell lattice of a water-soluble polymeric material with an average bead diameter in the range 0.2-5 mm. These beads are typically "emulsion-templated" materials formed by removal (by drying) of the water and oil from a continuous aqueous phase, in which the water-soluble polymeric material is dissolved, and a disperse oil phase respectively from a high internal phase emulsion. Such removal leaves a "skeletal" form of the emulsion behind "imprinted" into the water-soluble polymeric material. The beads dissolve rapidly in water and have the remarkable property that water-insoluble components incorporated into the emulsion (typically by their dissolution in the disperse oil phase) prior to drying can be dispersed in water on dissolution of the beads.

There are many instances where it would be desirable to provide water-insoluble materials in an aqueous environment either for direct use or for incorporation into a further product/process for onward use. Such water-insoluble materials include pharmaceuticals, nutraceuticals, animal health products, agrochemicals, biocidal compounds, food additives (including flavourings), polymers, proteins, peptides, cosmetic ingredients, coatings, inks/dyes/colourants, laundry or household cleaning and care products.

Similarly, there are instances where it would be desirable to provide water-soluble materials in a non-aqueous environment, again either for direct use or for incorporation into a further product/process for onward use. Such water-soluble materials include pharmaceuticals, nutraceuticals, animal health products, agrochemicals, biocidal compounds, food additives (including flavourings), polymers, proteins, peptides, cosmetic ingredients, coatings, inks/dyes/colourants, laundry or household cleaning and care products.

Throughout the specification, by a "water-soluble material" and like terms, we mean a material that forms a homogeneous solution in water. In the context of the present invention, "water-soluble" means that the solubility of the material in question in water at ambient temperature and pressure is at least 10 g/L. The term "water-soluble" includes the formation of structured aqueous phases as well as true ionic solution of molecularly mono-disperse species.

Conversely, by a "water-insoluble material" and like terms, we mean a material that forms a homogeneous solution in a non-aqueous medium, e.g. an organic solvent or oil. In the context of the present invention, "water-insoluble" means that the solubility of the material in question in water at ambient temperature and pressure is less than 10 g/L.

For the avoidance of any doubt, in the present application the term "ambient temperature" means 25° C. whilst "ambient pressure" means 1 atmosphere (101.325 kPa) of pressure.

As an example to illustrate the problem, prochloraz and λ-cyhalothrin are both active biocide materials (a foliar fungicide and a pyrethroid insecticide respectively) which are water-insoluble (0.039 g/L and 0.005 g/L at 20° C. respectively). It would be useful to be able to deliver both of these materials from an aqueous system/environment.

With this problem in mind, the inventors have previously devised what are known herein as "carrier liquids". These are compositions which are liquid at ambient temperature and pressure and contain a liquid-insoluble material (hereinafter referred to as a "dopant material") in a disperse, preferably nano-disperse, form. By "liquid-insoluble" it is meant that the dopant material is not normally soluble in the liquid, i.e. a solid body of the dopant material introduced into the liquid (in an amount of 1 mg/ml) will remain as such (i.e. solid) without dissolving. By "nano-disperse form" and like terms it is meant that the material in question is present in the carrier liquid as discrete nanoparticles of z-average diameter less than 1000 nm.

The present inventors previously discovered (as described and claimed in WO2006/079410A1) that such carrier liquids could be prepared by utilising a method comprising preparing an emulsion from a) an aqueous phase, b) a second liquid phase, which is volatile and immiscible with the aqueous phase, c) a carrier material, which is soluble in the continuous phase of the emulsion and liquid at ambient temperature, and d) a dopant material, which is soluble in the disperse phase of the emulsion, and subsequently cooling the emulsion until both the continuous phase and the carrier material become solid (i.e. they freeze), followed by removal of water and the volatile second phase from the cooled emulsion in vapour form to obtain a liquid product (at ambient temperature) with the dopant material dispersed therein.

Although this method is successful, there is however a need to improve upon it by simplifying the formation of the emulsion as the intermediate phase to be dried. The present inventors have now determined that an improvement to the known "emulsion method" can be obtained if a single solvent or a mixture of miscible solvents which comprise a single phase solution are used instead of mixtures of immiscible aqueous/non-aqueous solvents that would be used to form an emulsion.

SUMMARY

Accordingly, the present invention provides a novel method for the preparation of a carrier liquid which comprises the steps of:

(I) Preparing a Single Phase Solution Comprising:
    a) a solvent or a mixture of miscible solvents,
    b) a liquid carrier material, which is soluble in solvent (a), and
    c) a dopant material which is also soluble in solvent (a), (II) cooling the single phase solution produced in step (I) to a temperature at which at least both the solvent (a) and carrier material (b) become solid, and (III) removing solid solvent (a) from the cooled single phase solution in vapour form, such that the remaining cooled carrier material (b) and dopant material (c) are returned to ambient temperature thus providing a product of liquid carrier material (b) having dopant material (c) dispersed therein.

DETAILED DESCRIPTION

In the carrier liquids obtained by the above method of the present invention, the liquid carrier material (b) and the dopant material (c) are not present in the same phase after step (III); the dopant material is believed to be present as a nano-particle phase dispersed through a continuous phase of the liquid carrier material, i.e. that nano-sized particles of the dopant material are dispersed throughout the body of liquid carrier material.

For the avoidance of any doubt, throughout this specification by "liquid" and like terms it is meant the state of matter in which the substance in question exhibits (at a temperature above its solidification temperature but at or below 40° C.) a characteristic readiness to flow and relatively high incompressibility; the substance in question does not resist change of shape but does resist a change of size. Thus gels, waxes and other such "semi-solid" materials are to be considered (by virtue of the definition provided above) as substances which are "liquids" for the purposes of the present invention.

Many materials manifest in different states of matter from liquid to solid according to their average molecular weight, for example, polyethylene glycol (PEG) is available over a wide range of average molecular weights from 300 g/mol (i.e. approximately 300 Daltons) to 10,000,000 g/mol (i.e. approximately 10,000,000 Daltons). For example, PEG-200 and PEG-400 (having average molecular weights of ~200 g/mol and ~400 g/mol respectively) are non-volatile liquids at ambient temperature, PEG-600 (having an average molecular weight of ~600 g/mol and a melting temperature range of 17-22° C.) has a paste-like consistency at ambient temperature, whilst PEG-1500 (having an average molecular weight of ~1500 g/mol) is a solid at ambient temperature. For the avoidance of any doubt, a person skilled in the art would know to choose a liquid form of such a material for use in the present invention, and would know to discount those forms which are solid above 40° C.

Further to the definition provided above for "nano-disperse form", in the context of the present invention, "nano-particles" means particles having a z-average particle size of less than 1000 nm.

Preferably however, the z-average diameter of the nano-disperse form of the dopant material is in the range of from 10 to 800 nm, even more preferably in the range of from 10 to 700 nm, especially in the range of from 10 to 600 nm, and possibly in the range of from 20 to 600 nm.

The preferred method of particle sizing for the dispersed products of the present invention employs a Dynamic Light Scattering (DLS) instrument (Zetasizer Nano S, manufactured by Malvern Instruments UK). Specifically, the Malvern Instruments Nano S uses a red (633 nm) 4 mW Helium-Neon laser to illuminate a standard optical quality UV cuvette containing a suspension of the particles to be sized. The particle sizes quoted in this application are those obtained with that apparatus using the standard protocol provided by the instrument manufacturer. The size of the nano-particles in a carrier liquid obtained by the method of the present invention is measured once the liquid carrier material (with dopant material dispersed therein) has been dissolved by stirring in water or an organic solvent as appropriate, and in which the dopant is insoluble.

On return to ambient temperature, the previously solid (cooled) carrier material returns to its original liquid form. Surprisingly, the dispersed liquid-insoluble dopant material remains dispersed throughout the liquid carrier material, despite the fact that it would otherwise be insoluble in the carrier material and that the emulsion-templated structure previously thought to be essential is not present. An immediate benefit of provision of such a carrier liquid is its ability to be used "as is" without any requirement for dissolution/dispersion in a liquid medium prior to use. Consequently, a liquid product having a much higher concentration of dopant material (than may otherwise be obtained) is immediately achievable, with obvious immediate end uses, such as injectable forms of pharmaceuticals. Further surprisingly, if the carrier liquid is added to a further miscible liquid (which the dopant material is again insoluble in), the dopant material is able to readily disperse through the resulting miscible liquid mixture.

When a single solvent is used to form the single phase solution, this solvent may be aqueous or non-aqueous depending on the nature of both the liquid carrier material and the dopant material in question.

When a mixture of miscible solvents is used to form the single phase solution, at least one of the solvents is preferably an aqueous solvent and at least another solvent is preferably a non-aqueous solvent.

Such mixtures of solvents are not limited to binary mixtures, but can include three or more components. Additional solvents can be present provided that they are miscible in the solvent mixture as a whole. For the avoidance of doubt, whilst the liquid carrier material and the dopant material are both soluble in the single phase solution (which can be a single solvent or a mixture of solvents,) the use of an emulsion is not altogether excluded, as other materials may be present which are not miscible, provided that there exists at least one single phase which comprises both the liquid carrier material and the dopant material.

Where a mixture of solvents is used, it is not necessary that the solvents are mixed before the liquid carrier material and the dopant material are dissolved therein. It is possible to dissolve the liquid carrier material and the dopant material in different solvents, which are then mixed prior to the cooling step.

Preferably the solvent(s) present are removed simultaneously, rather than sequentially, in a single drying, preferably freeze-drying, step.

The present invention further provides:
(1) a water-soluble carrier liquid comprising a water-soluble liquid carrier material having a water-insoluble dopant material dispersed throughout in the form of nano-particles; and
(2) a water-insoluble carrier liquid comprising a water-insoluble liquid carrier material having a water-soluble dopant material dispersed throughout in the form of nano-particles.

Preferably the liquid carrier material comprised in the carrier liquid (being either water-soluble or water-insoluble) dissolves rapidly on contact with an appropriate medium (aqueous or non-aqueous respectively) even at ambient temperature, ambient pressure and at neutral pH, thereby releasing the nano-particles of dopant material into the medium to be dispersed. Preferably dissolution of the carrier liquid occurs in less than five minutes, more preferably less than three minutes, most preferably less than one minute.

The present invention yet further provides:
(1) nano-dispersions comprising a solution of water-soluble liquid carrier material having a water-insoluble dopant material nano-dispersed therein, formed by exposing to an aqueous medium a carrier liquid according to the present invention; and
(2) nano-dispersions comprising a solution of water-insoluble liquid carrier material having a water-soluble dopant material nano-dispersed therein, formed by exposing to a non-aqueous medium a carrier liquid according to the present invention.

In both cases, the dopant material is nano-dispersed when the carrier materials are dissolved in the appropriate medium. Nano-dispersion into said medium of such liquid-insoluble dopant materials is much improved.

Liquid Carrier Materials

The liquid carrier material used in the method of the invention may either be water-soluble (to enable provision of a water-insoluble dopant material in an aqueous environment) or water-insoluble (to enable provision of a water-soluble dopant material in a non-aqueous environment). In both cases, the liquid carrier material will be comprised in the single phase solution of step (I).

The liquid carrier material may be in the form of one or more liquid polymeric carrier materials (other than surfactants) and/or one or more liquid surfactant carrier materials.

Water-Soluble Liquid Carrier Materials

Suitable water-soluble liquid polymeric materials may be chosen from any one or more of the following which will be present in a liquid form (rather than a solid) at a low Degree of Polymerisation (specific to each polymer) which defines the average numbers of monomer units in a polymerised chain: homopolymers of or copolymers prepared from two or more monomers selected from: vinyl alcohol, acrylic acid, methacrylic acid, acrylamide, methacrylamide, acrylamide methylpropane sulphonates, aminoalkylacrylates, aminoalkyl-methacrylates, hydroxyethylacrylate, hydroxyethylmethylacrylate, vinyl pyrrolidone, vinyl imidazole, vinyl amines, ethyleneglycol and other alkylene glycols, ethylene oxide and other alkylene oxides, ethyleneimine, styrenesulphonates, ethyleneglycolacrylates and ethyleneglycol methacrylate.

When the polymeric material is a copolymer it may be a statistical copolymer (heretofore also known as a random copolymer), a block copolymer, a graft copolymer or a hyperbranched copolymer. Comonomers other than those listed above may also be included in addition to those listed if their presence does not destroy the water-soluble nature of the resulting liquid polymeric material.

Examples of suitable and preferred homopolymers include polyethylene glycol (PEG) having an average molecular weight of less than 1000 g/mol, polyethyleneimines (especially those available under the trade name Lupasol™ from BASF) and ethoxylated derivatives thereof.

PEG-400 and PEG-600 are particularly preferred polymeric liquid carrier materials.

For the avoidance of any doubt, if a polymeric liquid carrier material is used in the present invention, it will be without cross-linking because the purpose of the carrier material is to dissolve on contact with an aqueous/non-aqueous (as appropriate) medium. It is well known that cross-linking has a large effect on physical properties of a polymer because it restricts the relative mobility of the polymer chains, increases molecular weight and causes large scale network formation, thus preventing its dissolution capability. Polystyrene, for example, is soluble in many solvents such as benzene, toluene and carbon tetrachloride. Even with a small amount of cross-linking agent (divinylbenzene, 0.1%) however, the polymer no longer dissolves but only swells.

Suitable water-soluble liquid surfactant carrier materials may be non-ionic, anionic, cationic, amphoteric or zwitterionic. Again, an appropriate liquid surfactant carrier material may be chosen from any one or more of the following which will be present in a liquid form (rather than as a solid) with a person skilled in the art appreciating that only such liquid forms are intended for use within the scope of the present invention: ethoxylated triglycerides; fatty alcohol ethoxylates (for example Cremophor™ A type solubilizers); alkylphenol ethoxylates; fatty acid ethoxylates (for example Solutol™ HS15 and Cremophor™ EL type solubilizers); fatty amide ethoxylates; fatty amine ethoxylates; sorbitan alkanoates; ethylated sorbitan alkanoates; PEG-ylated sorbitan esters (available under the trade name Tween™); non-PEG-ylated sorbitan esters (available under the trade name Span™); alkyl ethoxylates; block copolymers of ethylene oxide and propylene oxide, i.e. poloxamers (available under the trade name Pluronics™); alkyl polyglucosides; alkyl polyglycol ethers (available under the trade name Brij™); stearol ethoxylates; alkyl polyglycosides; hydroxylated lecithins; aromatic ethoxylates (for example Triton X-15™ and Triton X-100™); D-alpha-tocopheryl polyethylene glycol 1000 succinate (vitamin E TPGS); sodium docusate (AOT).

Mixtures of any one or more of these liquid surfactants may be used, possibly in combination with one or more other water-soluble carrier materials.

The preferred surfactants are sodium docusate, Brij™ 30, Brij™ 93, Span™ 20, Span™ 80, Span™ 83, Span™ 85, Tween™ 20, Tween™ 40, Tween™ 60, Tween™ 65 and Tween™ 80, poloxamers (Pluronics™), fatty acid ethoxylates (for example Solutol™ HS15 and Cremophor™ EL type solubilizers), fatty alcohol ethoxylates (for example Cremophor™ A type solubilizers) and aromatic ethoxylates (for example Triton X-15™ and Triton X-100™).

In addition to the polymeric and surfactant carrier materials described above, liquid diols (for example propylene glycol), liquid triols (for example glycerol) and other liquid polyols are also suitable liquid carrier materials for use in the method of the present invention. Indeed, propylene glycol and glycerol are preferred liquid carrier materials of this type.

It is also within the scope of the present invention to provide a carrier liquid comprising a water-soluble liquid carrier material (as hereinbefore described) which further comprises one or more optional water-soluble solid carrier materials, with the proviso that upon any such addition of a solid carrier material(s) to the liquid carrier material, the liquid carrier material retains the characteristics of a liquid and does not become a solid. The amount of solid carrier material(s) that may be added to the liquid carrier material without detrimentally affecting its liquid characteristics will be judged by a skilled person on a case-by-case basis as the nature of each of the liquid carrier material and the one or more solid carrier materials being added will determine the ratio at which they can be mixed.

Preferably, the solid carrier material(s) will dissolve in the liquid carrier material, further preferably so as to form a homogeneous liquid solution.

Advantageously, up to 50% by weight of the carrier liquid formed by the method of the present invention may be solid carrier material(s), preferably up to 40% by weight, and more preferably up to 30% by weight.

Suitable water-soluble, solid carrier materials may be chosen from any one or more of the following: natural polymers, including guar gum, alginate, locust bean gum; polysaccharides including dextran; cellulose derivatives including xanthan gum, xyloglucan, cellulose acetate, methylcellulose, hydroxyethylcellulose, hydroxyethylmethylcellulose, hydroxypropylcellulose (HPC), hydroxypropylmethylcellulose (HPMC), carboxymethylcellulose and its salts (e.g. the sodium salt—SCMC), carboxymethylhydroxyethylcellulose and its salts (e.g. the sodium salt); cyclodextrins including β-cyclodextrin; polymers including polyvinyl alcohol (PVA), polyacrylic acid, polymethacrylic acid, polyacrylamides (such as poly-N-isopropylacrylamide), polymethacrylamide, polyacrylamines, polymethylacrylamines, (such as polydimethylaminoethylmethacrylate and poly-N-morpholinoethylmethacrylate), polyvinylpyrrolidone (PVP), polystyrenesulphonate, polyvinylimidazole, polyvinylpyridine, poly-2-ethyloxazoline; surfactants inlcuding dialkyl sulfosuccinates, soaps, alkyl sulfates, alkylether sulfates, alkylether carboxylates, alkylbenzene sulfonates, alkylether phosphates, sarcosinates, alkyl sulfonates, alkyl carboxylates, alkyl phosphates, paraffin sulfonates, secondary n-alkane sulfonates, α-olefin sulfonates; isethionate sulfonates.

For the avoidance of any doubt, it is acknowledged that some of the species identified above have both water-soluble and water-insoluble forms, e.g. cellulose acetate, the solubility of which is variable according to its degree of substitution (DS) with acetyl groups. However, for the purposes of the present invention, it should be understood that only the water-soluble forms of any such species are to be considered within the context of the above-identified list.

Water-Insoluble Liquid Carrier Materials

Suitable water-insoluble liquid carrier materials include squalene, natural oils, such as triglycerides, mineral oils, synthetic oils, vegetable oils, preferably avocado oil, rice bran oil, jojoba oil, Babassu oil, safflower seed oil, soybean oil, vitamin E, vitamin E acetate, non-vegetable oils such as silicone oils and paraffin oils, as well as waxes including carnauba wax, candelilla wax and lecithin. Mixtures of oils can be used. Other suitable water-insoluble liquid carrier materials are:
  siloxanes;
  fatty acids (for example, oleic acid);
  fatty alcohols;
  long chain (having a carbon chain length of at least C10) amines;
  linear or branched esters of fatty acids and alcohols (such as C12-C13 alkyl octanoate esters);
  esters of fatty acids and glycols (such as propylene glycol esters);
  esters of hydroxyfatty acids, including C12-C13 alkyl malate, C12-C13 alkyl lactate and C12-C13 alkyl citrate.
  Other esters such as diethylene glycol dioctanoate or diisononanate, propylene glycol dicaprylate, neopentyl glycol diheptanoate, etc., can be used.
  Suitable water-insoluble liquid polymeric materials include polyvinyl ethers, polyvinyl esters, polypropylene glycol and polyesters.
  Suitable and preferred water-insoluble liquid carrier materials are safflower seed oil, soybean oil, squalene, polypropylene glycol and paraffin oil.

It is also within the scope of the present invention to provide a carrier liquid comprising a water-insoluble liquid carrier material (as hereinbefore described) which further comprises one or more optional water-insoluble solid carrier materials, with the proviso that upon any such addition of a solid carrier material(s) to the liquid carrier material, the liquid carrier material retains the characteristics of a liquid and does not become a solid. Again, the amount of solid carrier material(s) that may be added to the liquid carrier material without detrimentally affecting its liquid characteristics will be judged by a skilled person on a case-by-case basis as the nature of each of the liquid carrier material and the one or more solid carrier materials being added will determine the ratio at which they can be mixed.

Preferably, the solid carrier material(s) will dissolve in the liquid carrier material, further preferably so as to form a homogeneous liquid solution.

Advantageously, up to 50% by weight of the carrier liquid formed by the method of the present invention may be solid carrier material(s), preferably up to 40% by weight, and more preferably up to 30% by weight.

Suitable water-insoluble, solid carrier materials may be chosen from any one or more of the following: polymethacrylates, polyacrylates, polycaprolactone (PCL), polystyrenics, polylactic acid, polyglycolic acid, ethyl cellulose, enteric polymers and copolymers thereof.

The water-insoluble liquid carrier material may furthermore contain lipophilic agents which are dissolved therein. These can be, for example:
  UV-blocking agents, such as octyl methoxycinnamate, octyl salicylate, menthyl anthranilate, octocrylene, benzophenone-3, octyl dimethyl p-aminobenzoic acid [PABA], 4-methylbenzilidene camphor, butyl methoxydibenzoyl methane;
  liposoluble vitamins, such as esters of vitamin A (e.g. retinol palmitate or acetate), esters of vitamin E (e.g. tocopherol acetate or tocopherol linolate), vitamin B2, vitamin D6, vitamin F;
  anti-inflammatory agents, such as bisabolol (also known as levomenol), glycerrethinic acid, stearyl glycerrhetinate;
  polyunsaturated fatty acids or esters thereof, such as avocado, peanut and borrage oils, jojoba oil, calendula oil;
  natural ingredients, such as shea butter, avocado oil, soybean oil;
  lanolin and its derivatives;
  emollients, such as perhydrosqualene, perfluoropolyethers.

Polyethylene glycol is preferred as a water-soluble polymeric carrier material for pharmaceutical applications due to its low toxicity. Other preferred examples of water-soluble carrier materials include glycerol and propylene glycol either alone or in combination with a liquid surfactant carrier material. Similarly, preferred water-insoluble carrier materials include safflower seed oil and vitamin E acetate.

Solvent(s)

The solvent or mixture of miscible solvents comprised in the single phase solution provided in the method of the invention may be selected from one or more of the following:
  alkanes, such as heptane, n-hexane, iso-octane, decane, dodecane;
  lower (C1-C10) alcohols, such as methanol, ethanol, propanol, isopropanol, butanol, isobutanol, tertiary butanol, 1-pentanol;
  organic acids, such as formic acid, acetic acid;
  amides, such as formamide, N,N-dimethylformamide;
  nitriles, such as acetonitrile;
  cyclic hydrocarbons, such as toluene, xylene, cyclohexane;
  halogenated alkanes, such as dichloromethane, dichoroethane, trichloromethane (chloroform), fluorotrichloromethane, tetrachloroethane;
  esters, such as ethyl acetate;
  aldehydes and ketones, such as acetone, 2-butanone, 2-hexanone;
  ethers, such as diethyl ether;

volatile cyclic silicones, such as cyclomethicones containing from 4 to 6 silicon atoms, e.g. Dow Corning 245 Fluid and Dow Corning 345 Fluid, available from Dow Corning Inc.;

water.

Particularly preferred solvents are acetonitrile and/or tertiary butanol (with water), cyclohexane and chloroform. The freezing point of cyclohexane is higher than that of water and the specific heat capacity for cyclohexane is much lower than that of water. It is believed that this assists rapid freezing of the single phase solution.

Dopant Materials

As described above, the dopant material is liquid-insoluble, i.e. insoluble in the liquid carrier material. Thus water-insoluble dopant materials are to be used with water-soluble carrier materials, whilst water-soluble dopant materials are to be used with water-insoluble carrier materials. As the carrier material is incorporated into the body of the single phase solution, so the dopant material is incorporated therein. Of course, it may also be that either of these combinations also includes a further oppositely soluble dopant material, e.g. the combination of water-soluble liquid carrier material having a water-insoluble dopant material therein may also contain a water-soluble dopant material.

Water-soluble dopant materials may therefore be incorporated into water-insoluble liquids by incorporating them into the solvent or one or more of the solvents in the mixture of solvents comprised in the single phase solution, which is then preferably freeze-dried. In the alternative, water-insoluble dopant materials may be incorporated into water-soluble liquids by incorporating them into the solvent or one or more of the solvents in the mixture of solvents comprised in the single phase solution, which is then preferably freeze-dried.

Suitable water-insoluble dopant materials include:

antimicrobial agents, for example triclosan, climbazole, octapyrox, ketoconizole, phthalimoperoxyhexanoic acid (PAP), certain quaternary ammonium compounds, colloidal silver, zinc oxide;

antidandruff agents, for example zinc pyrithione;

skin lightening agents, for example 4-ethylresorcinol;

fluorescing agents, for example 2,5-bis(2-benzoxazolyl) thiophene for use on fabrics (such as cotton, nylon, polycotton or polyester) in laundry products;

skin conditioning agents, for example cholesterol;

antifoaming agents, for example isoparaff in;

hair conditioning agents, for example quaternary ammonium compounds, protein hydrolysates, peptides, ceramides, hydrophobic conditioning oils (for example hydrocarbon oils such as paraffin oils and/or mineral oils, fatty esters such as mono-, di-, and tri-glycerides, silicone oils such as polydimethylsiloxanes (e.g. dimethicone) and mixtures thereof);

fabric conditioning agents, for example quaternary ammonium compounds having 1 to 3, preferably 2, optionally substituted (C8-C24) alk(en)yl chains attached to the nitrogen atom by one or more ester groups, hydrophobic monoparticles such as a sucrose polyester, for example sucrose tetra-tallowate, silicones, for example polydimethylsiloxane;

thickening agents, for example hydrophobically modified cellulose ethers such as modified hydroxyethylcelluloses;

dyes, for example dyes intended to change the colour of fabrics, fibres, skin or hair;

UV-protecting agents, such as sunscreens, for example octyl methoxycinnamate (Parsol MCX), butyl methoxydibenzoylmethane (Parsol 1789) and benzophenone-3 (Uvinul M-40), ferulic acid;

bleach or bleach precursors, for example 6-N-phthalimidoperoxyhexanoic acid (PAP) or photobleaching compounds;

antioxidants, for example hydrophobic vitamins such as vitamin E, retinol, antioxidants based on hydroxytoluene such as Irganox™ or commercially available antioxidants such as the Trollox™ series;

biocides, for example fungicides, algicides, mollusicides, miticides, rodenticides, insecticides, pesticides, herbicides that are stored as solid compositions before use but which are made up into liquid for spraying onto animals or crops;

perfumes or flavourings, or precursors thereto;

pharmaceutically or veterinary active materials, for example sartans, statins, opioids, non-steroidal anti-inflammatory drugs (NSAIDs); and vitamins and nutraceuticals.

Suitable water-soluble dopant materials include:

amino acids, for example arginine and alanine;

water-soluble fluorescers, for example Tinopal CBSX;

water-soluble vitamins, for example vitamin C;

water-soluble food additives, for example sodium saccharin, citric acid, sodium chloride;

water-soluble agrochemicals, for example glyphosate;

water-soluble dyes, for example methyl orange;

water-soluble pharmaceuticals, for example emtricitabine;

water-soluble bleaches;

dental/oral health ingredients, for example sodium monophosphate; and anti-microbial ingredients, for example tetracycline.

Use of the carrier liquids obtained by the novel method of the present invention facilitates dispersion, and in many cases enables more effective dispersion, of otherwise insoluble dopant materials than was previously believed to be possible by a simpler method than previously devised.

Furthermore, the carrier liquids obtained by the present invention may be used to introduce water-soluble or water-insoluble dopant materials into products, including during the manufacture of said products.

Moreover, the carrier liquids obtained by the present invention may be used to transport materials to sites where they can be subsequently incorporated into products.

Other benefits of the present invention includes that the carrier liquid containing the dispersed dopant material provides a concentrated nanodispersion of the dopant material that can be used without any further dilution being necessary, i.e. the carrier liquid per se can be used without having to be added to a solvent, e.g. water, to obtain the required nanodispersion. The dopant material can be incorporated in the carrier liquid in varying concentrations, for example from around 10% by weight of the liquid carrier material up to around 50% by weight.

Some specific examples of products in which the carrier liquids obtained by the present invention may be used are given below. It should be understood that these are given as examples only and are not intended to limit the applicability of the present invention. Examples of circumstances in which the carrier liquids obtained by the present invention may be used to incorporate a water-insoluble material into a product during the manufacture of that product include:

the introduction of water-insoluble materials such as fluorescers, enzymes, bleaches, hydrophobic polymers, for example hydrophobically modified polyacrylates, silicones, hydrophobically modified polyvinylpyrrolidone, sulpho alkyl polysaccharides, Jaguar™ and JR polymers, fatty alcohols or acids, dyes for example shading dyes or black dyes for colour recovery into laundry products;

the introduction of water-insoluble dyes in the process of manufacturing water-soluble inkjet compositions;

the introduction of different water-insoluble materials to enable a manufacturer to produce a single base formulation into which the desired water-insoluble materials may be introduced by the use of an appropriate carrier liquids obtained by the present invention;

the introduction of water-insoluble pharmaceuticals in the process of manufacturing pharmaceutical preparations suitable for, e.g. topical, oral, respiratory and/or parenteral administration.

In addition to the normally liquid-insoluble dopant material, the carrier liquids obtained by the method of the present invention may also include dopant materials that are soluble in the carrier liquid.

Method of Preparation

An intermediate single phase solution required by the method of the present invention may typically be prepared under conditions which are well known to those skilled in the art, for example, by using a magnetic stirring bar, a homogenizer, or a rotator mechanical stirrer.

Cooling of the single phase solution may be accomplished by introducing the single phase solution into a fluid freezing medium, either directly (for example by pouring, dropping or spraying) or indirectly (for example, when in a mould). Preferably, the freezing medium is at a temperature below the freezing point of all components of the single phase solution, and is preferably at a much lower temperature to facilitate rapid freezing.

The freezing medium is preferably a liquefied substance, which is a gas or vapour at ambient temperature and pressure. The freezing medium may be at its boiling point during the freezing of the liquid medium or it may be cooled to below its boiling point by external cooling means.

The fluid freezing medium may be selected from one or more of the following group:

liquid air (boiling point: −196° C.);
liquid nitrogen (boiling point: −196° C.);
liquid ammonia (boiling point: −33° C.);
liquified noble gas, such as argon (boiling point: −186° C.);
liquefied halogenated hydrocarbon, such as trichloroethylene;
chlorofluorocarbons, such as Freon™;
hydrocarbons, such as hexane, dimethylbutene, isoheptane, cumene.

Mixtures of organic liquids and solid carbon dioxide may also be used as the fluid freezing medium. Examples of suitable mixtures include chloroform or acetone with solid carbon dioxide, and diethyl ether with solid carbon dioxide.

Due to its very low boiling temperature, unreactivity, ease of expulsion and economy, liquid nitrogen is a preferred fluid freezing medium.

Alternatively, cooling of the single phase solution may be accomplished by placing the single phase solution (typically in a container, for example a mould) into a freezing environment, such as a freezer, which may be at a temperature of approximately −50° C. The freezing environment may be a freeze-dryer, in which case, both the cooling (freezing) of the single phase solution and the subsequent removal of solid solvent in vapour form may occur in the one (and the same) environment.

The solvent or mixture of miscible solvents comprised in the single phase solution may be removed from the frozen single phase solution by exposing it to high vacuum (for example around 100 mPa). The conditions for freeze drying will be well known to those skilled in the art; the vacuum to be applied and the time taken should be such that effectively all of the solvent or mixture of solvents present is removed by sublimation. Preferably the solvent(s) removed during freeze-drying are captured for re-use.

Freeze-drying may take place with the frozen single phase solution still in a mould (should a mould have been used as a vessel in which to freeze the solution). Alternatively, the frozen single phase solution may be removed from the mould and subsequently freeze-dried. The freeze-drying step may be performed for up to around 72 hours, sometimes around 48 hours, and preferably for less than 12 hours.

In a preferred method in accordance with the invention, the single phase solution comprises a mixture of at least one relatively volatile organic solvent and water, the mixture containing a less volatile water-soluble liquid carrier material and a water-insoluble dopant material. When this single phase solution is freeze-dried and the product thereby returned to ambient temperature, the product is a water-soluble liquid carrier liquid having a water-insoluble, often solid, dopant material nano-dispersed therein.

For a better understanding, the present invention will now be more particularly described by way of non-limiting examples only.

Example 1

10 wt % dichlorophen (anticestodal dopant material)
10 wt % polyoxyethylene (20) sorbitan monooleate (available under the trade name Tween™ 80) (liquid carrier material 1—non-ionic surfactant)
80 wt % polyethylene glycol 400 (PEG-400) (liquid carrier material 2—polymer)

5 mg of dichlorophen was dissolved in 0.5 ml of acetonitrile forming solution (a), whilst 5 mg of Tween™ 80 and 40 mg of PEG-400 were dissolved in 0.5 ml of deionised water forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 μbar over a condenser maintained at −105° C.

The resultant solvent-free liquid product was dispersed into 1 ml of deionised water using a vortex bench-top mixer prior to analysis in triplicate via DLS (using a Malvern Zetasizer Nano S). The z-average particle size of the dichlorophen particles in the opaque/translucent dispersion was determined to be 199 nm.

Example 2

10 wt % dichlorophen (anticestodal dopant material)
10 wt % glycerin (liquid carrier material 1—polyol)
80 wt % polyoxyethylene (20) sorbitan monooleate (available under the trade name Tween™ 80) (liquid carrier material 1—non-ionic surfactant)

5 mg of dichlorophen was dissolved in 0.5 ml of acetonitrile forming solution (a), whilst 5 mg of glycerin and 40 mg of Tween™ 80 were dissolved in 0.5 ml of deionised water forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 μbar over a condenser maintained at −105° C.

The resultant solvent-free liquid product was dispersed into 1 ml of deionised water using a vortex bench-top mixer prior to analysis in triplicate via DLS (using a Malvern Zetasizer Nano S). The z-average particle size of the dichlorophen particles in the opaque/translucent dispersion was determined to be 115 nm.

Example 3

10 wt % dichlorophen (anticestodal dopant material)
10 wt % octyl phenol ethoxylate (available under the trade name Triton X-100™) (liquid carrier material 1—non-ionic surfactant)
80 wt % glycerin (liquid carrier material 2—polyol)

5 mg of dichlorophen was dissolved in 0.5 ml of acetonitrile forming solution (a), whilst 5 mg of Triton X-100™ and 40 mg of glycerin were dissolved in 0.5 ml of deionised water forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of deionised water using a vortex bench-top mixer prior to analysis in triplicate via DLS (using a Malvern Zetasizer Nano S). The z-average particle size of the dichlorophen particles in the opaque/translucent dispersion was determined to be 191 nm.

Example 4

10 wt % prochloraz (fungicide dopant material)
10 wt % polyoxyethylene (20) sorbitan monooleate (available under the trade name Tween™ 80) (liquid carrier material 1—non-ionic surfactant)
80 wt % polyethylene glycol 400 (PEG-400) (liquid carrier material 2—polymer)

5 mg of prochloraz was dissolved in 0.5 ml of acetonitrile forming solution (a), whilst 5 mg of Tween™ 80 and 40 mg of PEG-400 were dissolved in 0.5 ml of deionised water forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of deionised water using a vortex bench-top mixer prior to analysis in triplicate via DLS (using a Malvern Zetasizer Nano S). The z-average particle size of the prochloraz particles in the opaque/translucent dispersion was determined to be 271 nm.

Example 5

10 wt % prochloraz (fungicide dopant material)
10 wt % polyethoxylated castor oil (available under the trade name Chremophor EL™ from BASF Corp) (liquid carrier material 1—non-ionic surfactant)
80 wt % polyethylene glycol 400 (PEG-400) (liquid carrier material 2—polymer)

5 mg of prochloraz was dissolved in 0.5 ml of acetonitrile forming solution (a), whilst 5 mg of polyethoxylated castor oil and 40 mg of PEG-400 were dissolved in 0.5 ml of deionised water forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of deionised water using a vortex bench-top mixer prior to analysis in triplicate via DLS (using a Malvern Zetasizer Nano S). The z-average particle size of the prochloraz particles in the opaque/translucent dispersion was determined to be 142 nm.

Example 6

10 wt % prochloraz (fungicide dopant material)
10 wt % polyethoxylated castor oil (available under the trade name Chremophor EL™ from BASF Corp) (liquid carrier material 1—non-ionic surfactant)
80 wt % glycerin (liquid carrier material 2—polyol)

5 mg of prochloraz was dissolved in 0.5 ml of acetonitrile forming solution (a), whilst 5 mg of Chremophor EL™ and 40 mg of glycerin were dissolved in 0.5 ml of deionised water forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of deionised water using a vortex bench-top mixer prior to analysis in triplicate via DLS (using a Malvern Zetasizer Nano S). The z-average particle size of the prochloraz particles in the opaque/translucent dispersion was determined to be 196 nm.

Example 7

10 wt % λ-cyhalothrin (insecticide dopant material)
90 wt % polyoxyethylene-polyoxypropylene block copolymer (available under the trade name Pluronic™ F68 from BASF Corp) (liquid carrier material—non-ionic surfactant)

25 mg of λ-cyhalothrin and 225 mg of Pluronic™ F68 were dissolved in 5 ml of chloroform in a vial to form a single phase solution, which was frozen in liquid nitrogen and subsequently freeze-dried (using a Christ Alpha 2-4 LSC bench-top freeze-dryer) for 48 hours at a pressure of 80 µbar over a condenser maintained at −85° C.

The resultant solvent-free waxy product was dispersed at a concentration of 1 mg/ml into deionised water using a vortex bench-top mixer prior to analysis in triplicate via DLS (using a Malvern Zetasizer Nano S). The z-average particle size of the λ-cyhalothrin particles in the opaque/translucent dispersion was determined to be 66 nm.

Example 8

20 wt % λ-cyhalothrin (insecticide dopant material)
40 wt % polyoxyethylene-polyoxypropylene block copolymer (available under the trade name Pluronic™ F127 from BASF Corp) (liquid carrier material 1—non-ionic surfactant)
40% polyethylene glycol 1000 (PEG-1000) (liquid carrier material 2—polymer)

50 mg of λ-cyhalothrin, 100 mg of Pluronic™ F127 and 100 mg of PEG-1000 were dissolved in 5 ml of chloroform in a vial to form a single phase solution, which was frozen in liquid nitrogen and subsequently freeze-dried (using a Christ Alpha 2-4 LSC bench-top freeze-dryer) for 48 hours at a pressure of 80 μbar over a condenser maintained at −85° C.

The resultant solvent-free waxy product was dispersed at a concentration of 1 mg/ml into deionised water using a vortex bench-top mixer prior to analysis in triplicate via DLS (using a Malvern Zetasizer Nano S). The z-average particle size of the λ-cyhalothrin particles in the opaque/translucent dispersion was determined to be 95 nm.

Example 9

10 wt % λ-cyhalothrin (insecticide dopant material)

30 wt % polyoxyethylene-polyoxypropylene block copolymer (available under the trade name Pluronic™ F127 from BASF Corp) (liquid carrier material 1—non-ionic surfactant)

30 wt % polyoxyethylene-polyoxypropylene block copolymer (available under the trade name Pluronic™ F68 from BASF Corp) (liquid carrier material 2—non-ionic surfactant)

30% polyethylene glycol 1000 (PEG-1000) (liquid carrier material 3—polymer)

25 mg of λ-cyhalothrin, 75 mg of Pluronic™ F127, 75 mg of Pluronic™ F68 and 75 mg of PEG-1000 were dissolved in 5 ml of chloroform in a vial to form a single phase solution, which was frozen in liquid nitrogen and subsequently freeze-dried (using a Christ Alpha 2-4 LSC bench-top freeze-dryer) for 48 hours at a pressure of 80 μbar over a condenser maintained at −85° C.

The resultant solvent-free waxy product was dispersed at a concentration of 1 mg/ml into deionised water using a vortex bench-top mixer prior to analysis in triplicate via DLS (using a Malvern Zetasizer Nano S). The z-average particle size of the λ-cyhalothrin particles in the opaque/translucent dispersion was determined to be 52 nm.

Example 10

15 wt % ibuprofen (NSAID dopant material)

8 wt % polyoxyethylene (20) sorbitan monopalmitate (available under the trade name Tween™ 40) (liquid carrier material 1—non-ionic surfactant)

50% polyethylene glycol 400 (PEG-400) (liquid carrier material 1—polymer)

27 wt % polyvinyl alcohol (MW: 10,000 Da) (additional (solid) carrier material—polymer)

0.15 g of ibuprofen was dissolved in 10 ml of ethanol forming solution (a), whilst 0.27 g of polyvinyl alcohol, 0.08 g of Tween™ 40 and 0.5 g of PEG-400 were dissolved in 20 ml of deionised water forming solution (b). Solutions (a) and (b) were combined in a vial to form a single phase solution, which was frozen in liquid nitrogen and subsequently freeze-dried (using a VirTis Advantage bench-top freeze-dryer) for 36 hours at a pressure of 40 μbar over a condenser maintained at −105° C.

The resultant viscous liquid/gel was dispersed at a concentration of 2 mg/ml into deionised water using a vortex bench-top mixer prior to analysis in triplicate via DLS (using a Malvern Zetasizer Nano S). The z-average particle size of the ibuprofen particles was determined to be 112 nm.

Example 11

15 wt % ibuprofen (NSAID dopant material)

6 wt % polyoxyethylene-polyoxypropylene block copolymer (available under the trade name Pluronic™ F127 from BASF Corp) (liquid carrier material 1—non-ionic surfactant)

50% polyethylene glycol 300 (PEG-300) (liquid carrier material 1—polymer)

29 wt % hydroxypropylmethylcellulose (HPMC) (additional (solid) carrier material—polymer)

0.15 g of ibuprofen was dissolved in 10 ml of ethanol forming solution (a), whilst 0.29 g of HPMC, 0.06 g of Pluronic™ F127 and 0.5 g of PEG-300 were dissolved in 20 ml of deionised water forming solution (b). Solutions (a) and (b) were combined in a vial to form a single phase solution, which was frozen in liquid nitrogen and subsequently freeze-dried (using a VirTis Advantage bench-top freeze-dryer) for 36 hours at a pressure of 40 μbar over a condenser maintained at −105° C.

The resultant viscous liquid/gel was dispersed at a concentration of 2 mg/ml into deionised water using a vortex bench-top mixer prior to analysis in triplicate via DLS (using a Malvern Zetasizer Nano S). The z-average particle size of the ibuprofen particles was determined to be 86 nm.

Example 12

10 wt % sodium saccharin (food additive dopant material)

30 wt % safflower seed oil (liquid carrier material 1—natural oil)

60 wt % polyoxyethylene (4) lauryl ether (available under the trade name Brij™ 30 from Sigma-Aldrich) (liquid carrier material 2—non-ionic surfactant)

2 mg of sodium saccharin was dissolved in 0.1 ml of water forming solution (a), whilst 12 mg of Brij™ 30 and 6 mg of safflower seed oil were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 μbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the sodium saccharin particles in the clear/transparent dispersion was determined to be 717 nm.

Example 13

10 wt % sodium saccharin (food additive dopant material)

30 wt % octyl phenol ethoxylate (available under the trade name Triton™ X-15 from Sigma-Aldrich) (liquid carrier material 1—non-ionic surfactant)

60 wt % polyoxyethylene (4) lauryl ether (available under the trade name Brij™ 30 from Sigma-Aldrich) (liquid carrier material 2—non-ionic surfactant)

2 mg of sodium saccharin was dissolved in 0.1 ml of water forming solution (a), whilst 12 mg of Brij™ 30 and 6 mg of Triton™ X-15 were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 μbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the sodium saccharin particles in the clear/transparent dispersion was determined to be 678 nm.

Example 14

10 wt % sodium saccharin (food additive dopant material)
30 wt % sorbitan monododecanoate (available under the trade name Span™ 20 from Croda) (liquid carrier material 1—non-ionic surfactant)
60 wt % polyoxyethylene (4) lauryl ether (available under the trade name Brij™ 30 from Sigma-Aldrich) (liquid carrier material 2—non-ionic surfactant)

2 mg of sodium saccharin was dissolved in 0.1 ml of water forming solution (a), whilst 12 mg of Brij™ 30 and 6 mg of Span™ 20 were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the sodium saccharin particles in the clear/transparent dispersion was determined to be 654 nm.

Example 15

10 wt % sodium saccharin (food additive dopant material)
30 wt % sorbitan monododecanoate (available under the trade name Span™ 20 from Croda) (liquid carrier material 1—non-ionic surfactant)
60 wt % polyoxyethylene (2) oleyl ether (available under the trade name Brij™ 93 from Sigma-Aldrich) (liquid carrier material 2—non-ionic surfactant)

2 mg of sodium saccharin was dissolved in 0.1 ml of water forming solution (a), whilst 12 mg of Brij™ 93 and 6 mg of Span™ 20 were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the sodium saccharin particles in the cloudy/opaque dispersion was determined to be 764 nm.

Example 16

10 wt % citric acid (food additive dopant material)
30 wt % octyl phenol ethoxylate (available under the trade name Triton™ X-15 from Sigma-Aldrich) (liquid carrier material 1—non-ionic surfactant)
60 wt % polyoxyethylene (2) oleyl ether (available under the trade name Brij™ 93 from Sigma-Aldrich) (liquid carrier material 2—non-ionic surfactant)

2 mg of citric acid was dissolved in 0.1 ml of water forming solution (a), whilst 12 mg of Brij™ 93 and 6 mg of Triton™ X-15 were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 319 nm.

Example 17

10 wt % citric acid (food additive dopant material)
90 wt % sorbitan trioleate (available under the trade name Span™ 85 from Sigma-Aldrich) (liquid carrier material—non-ionic surfactant)

2 mg of citric acid was dissolved in 0.1 ml of water forming solution (a), whilst 18 mg of Span™ 85 was dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the cloudy/opaque dispersion was determined to be 262 nm.

Example 18

10 wt % citric acid (food additive dopant material)
60 wt % octyl phenol ethoxylate (available under the trade name Triton™ X-15 from Sigma-Aldrich) (liquid carrier material 1—non-ionic surfactant)
30 wt % polyoxyethylene (2) oleyl ether (available under the trade name Brij™ 93 from Sigma-Aldrich) (liquid carrier material 2—non-ionic surfactant)

2 mg of citric acid was dissolved in 0.1 ml of water forming solution (a), whilst 12 mg of Triton™ X-15 and 6 mg of Brij™ 93 were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the cloudy/opaque dispersion was determined to be 419 nm.

Example 19

18.5 wt % citric acid (food additive dopant material)
27.3 wt % polyoxyethylene (4) lauryl ether (available under the trade name Brij™ 30 from Sigma-Aldrich) (liquid carrier material 1—non-ionic surfactant)
54.5 wt % polyoxyethylene (2) oleyl ether (available under the trade name Brij™ 93 from Sigma-Aldrich) (liquid carrier material 2—non-ionic surfactant)

4 mg of citric acid was dissolved in 0.2 ml of water forming solution (a), whilst 12 mg of Brij™ 93 and 6 mg of Brij™ 30 were dissolved in 0.9 ml of acetonitrile forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 186 nm.

Example 20

18.5 wt % citric acid (food additive dopant material)
27.3 wt % polyoxyethylene (2) oleyl ether (available under the trade name Brij™ 93 from Sigma-Aldrich) (liquid carrier material 1—non-ionic surfactant)
54.5 wt % octyl phenol ethoxylate (available under the trade name
Triton™ X-15 from Sigma-Aldrich) (liquid carrier material 2—non-ionic surfactant)

4 mg of citric acid was dissolved in 0.2 ml of water forming solution (a), whilst 12 mg of Triton™ X-15 and 6 mg of Brij™ 93 were dissolved in 0.9 ml of acetonitrile forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 131 nm.

Example 21

18.5 wt % sodium chloride (food additive dopant material)
27.3 wt % polyoxyethylene (20) sorbitan tristearate (available under the trade name Tween™ 65 from Sigma-Aldrich) (liquid carrier material 1—non-ionic surfactant)
54.5 wt % octyl phenol ethoxylate (available under the trade name Triton™ X-15 from Sigma-Aldrich) (liquid carrier material 2—non-ionic surfactant)

4 mg of sodium chloride was dissolved in 0.2 ml of water forming solution (a), whilst 12 mg of Triton™ X-15 and 6 mg of Tween™ 65 were dissolved in 0.9 ml of acetonitrile forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the sodium chloride particles in the cloudy/opaque dispersion was determined to be 764 nm.

Example 22

10 wt % citric acid (food additive dopant material)
30 wt % soybean oil (liquid carrier material 1—natural oil)
60 wt % polyoxyethylene (4) lauryl ether (available under the trade name Brij™ 30 from Sigma-Aldrich) (liquid carrier material 2—non-ionic surfactant)

2 mg of citric acid was dissolved in 0.1 ml of water forming solution (a), whilst 12 mg of Brij™ 30 and 6 mg of soybean oil were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 225 nm.

Example 23

10 wt % citric acid (food additive dopant material)
30 wt % soybean oil (liquid carrier material 1—natural oil)
60 wt % sorbitan trioleate (available under the trade name Span™ 85 from Sigma-Aldrich) (liquid carrier material 2—non-ionic surfactant)

2 mg of citric acid was dissolved in 0.1 ml of water forming solution (a), whilst 12 mg of Span™ 85 and 6 mg of soybean oil were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 491 nm.

Example 24

10 wt % citric acid (food additive dopant material)
30 wt % safflower seed oil (liquid carrier material 1—natural oil)
60 wt % polyoxyethylene (4) lauryl ether (available under the trade name Brij™ 30 from Sigma-Aldrich) (liquid carrier material 2—non-ionic surfactant)

2 mg of citric acid was dissolved in 0.1 ml of water forming solution (a), whilst 12 mg of Brij™ 30 and 6 mg of safflower seed oil were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 µbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 259 nm.

Example 25

10 wt % citric acid (food additive dopant material)
30 wt % octyl phenol ethoxylate (available under the trade name Triton™ X-15 from Sigma-Aldrich) (liquid carrier material 1—non-ionic surfactant)
60 wt % safflower seed oil (liquid carrier material 2—natural oil)

2 mg of citric acid was dissolved in 0.1 ml of water forming solution (a), whilst 12 mg of safflower seed oil and 6 mg of Triton™ X-15 were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 μbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 326 nm.

Example 26

10 wt % citric acid (food additive dopant material)
30 wt % polyoxyethylene (4) lauryl ether (available under the trade name Brij™ 30 from Sigma-Aldrich) (liquid carrier material 1—non-ionic surfactant)
60 wt % safflower seed oil (liquid carrier material 2—natural oil)

2 mg of citric acid was dissolved in 0.1 ml of water forming solution (a), whilst 12 mg of safflower seed oil and 6 mg of Brij™ 30 were dissolved in 0.9 ml of tertiary butanol forming solution (b). Solutions (a) and (b) were combined in a vial to form a single phase solution, which was frozen in liquid nitrogen and subsequently freeze-dried (using a VirTis BTK bench-top freeze-dryer) for 48 hours at a pressure of 40 μbar over a condenser maintained at −105° C.

The resultant solvent-free liquid product was dispersed into 1 ml of isopropyl alcohol using a vortex bench-top mixer for 20 seconds prior to analysis in triplicate via DLS (using a Malvern Zetasizer Nano S). The z-average particle size of the citric acid particles in the clear/transparent dispersion was determined to be 624 nm.

The invention claimed is:

1. A method for the preparation of a carrier liquid which comprises the steps of:
   (I) preparing a single phase solution comprising:
      a) a solvent or a mixture of miscible solvents,
      b) a liquid carrier material, which is soluble in solvent (a), and
      c) a dopant material which is also soluble in solvent (a), wherein the solvent or the mixture of miscible solvents (a) is relatively more volatile than the liquid carrier material (b) and the dopant material (c),
   (II) cooling the single phase solution produced in step (I) to a temperature at which at least both the solvent (a) and carrier material (b) become solid, and
   (III) removing solid solvent (a) from the cooled single phase solution in vapour form, such that the remaining cooled carrier material (b) and dopant material (c) are returned to ambient temperature thus providing a product of liquid carrier material (b) having dopant material (c) dispersed therein.

2. A method according to claim 1 wherein cooling of the single phase solution is accomplished by introducing the single phase solution into a fluid-freezing medium, either directly or indirectly.

3. A method according to claim 1 wherein the solvent or mixture of miscible solvents is removed from the cooled single phase solution by exposing it to high vacuum.

4. A method according to claim 3 wherein the solvent removal step includes a freeze-drying process.

5. A method according to claim 1 wherein the solvent or mixture of miscible solvents is selected from one or more of the following: alkanes, C1-C10 alcohols, organic acids, amides, nitriles, cyclic hydrocarbons, halogenated alkanes, esters, aldehydes and ketones, ethers, volatile cyclic silicones and water.

6. A method according to claim 1 wherein the liquid carrier material is one or more liquid polymeric carrier materials and/or one or more liquid surfactant carrier materials.

7. A method according to claim 6 wherein the liquid carrier material is a water-soluble liquid polymeric material chosen from any one or more of: homopolymers of or copolymers prepared from two or more monomers selected from: vinyl alcohol, acrylic acid, methacrylic acid, acrylamide, methacrylamide, acrylamide methylpropane sulphonates, aminoalkylacrylates, aminoalkyl-methacrylates, hydroxyethylacrylate, hydroxyethylmethacrylate, vinyl pyrrolidone, vinyl imidazole, vinyl amines, ethyleneglycol and other alkylene glycols, ethylene oxide and other alkylene oxides, ethyleneimine, styrenesulphonates, ethyleneglycolacrylates and ethyleneglycol methacrylate.

8. A method according to claim 7 wherein the water-soluble liquid polymeric material is chosen from any one or more of the following: polyethylene glycol (PEG) having an average molecular weight of less than 1000 g/mol, polyethyleneimines and ethoxylated derivatives of polyethyleneimines.

9. A method accordingly to claim 6 wherein the liquid carrier material is a surfactant chosen from any one or more of the following: ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; PEG-ylated sorbitan esters; non-PEG-ylated sorbitan esters; alkyl ethoxylates; block copolymers of ethylene oxide and propylene oxide, i.e. poloxamers; alkyl polyglucosides; alkyl polyglycol ethers; stearol ethoxylates; alkyl polyglycosides; hydroxylated lecithins; aromatic ethoxylates; D-alpha-tocopheryl polyethylene glycol 1000 succinate (vitamin E TPGS) and sodium docusate (AOT).

10. A method according to claim 9 wherein the surfactant is chosen from any one or more of the following: sodium docusate, alkyl polyglycol ethers, non-PEG-ylated sorbitan esters, PEG-ylated sorbitan esters, poloxamers, fatty acid ethoxylates, fatty alcohol ethoxylates and aromatic ethoxylates.

11. A method according to claim 6 wherein the liquid carrier material is a water-insoluble material chosen from any one or more of the following: squalene, natural oils, mineral oils, synthetic oils, vegetable oils, avocado oil, rice bran oil, jojoba oil, Babassu oil, safflower seed oil, soybean oil, vitamin E, vitamin E acetate, non-vegetable oils, waxes, lecithin, and polymeric materials.

12. A method according to claim 11 wherein the liquid carrier material is chosen from any one or more of the following: safflower seed oil, soybean oil, squalene, polypropylene glycol and paraffin oil.

13. A method according to claim 1 wherein the dopant material is one or more selected from the following group of water-insoluble materials: antimicrobial agents, antidandruff agents, skin lightening agents, fluorescing agents, skin conditioning agents, antifoaming agents, hair conditioning agents, fabric conditioning agents, thickening agents, dyes, UV-protecting agents, bleach or bleach precursors, antioxidants, biocides, perfumes or precursors thereto, flavourings or precursors thereto, pharmaceutically or veterinary active materials, vitamins and nutraceuticals.

14. A method according to claim 1 wherein the dopant material is one or more selected from the following group of water-soluble materials: amino acids, water-soluble fluorescers, water-soluble vitamins, water-soluble food additives, water-soluble agrochemicals, water-soluble dyes, water-soluble pharmaceuticals, water-soluble bleaches, dental/oral health ingredients and anti-microbial ingredients.

15. A method according to claim 1 wherein the dopant material is present as a nano-particle phase dispersed through a continuous phase of the liquid carrier material.

16. A method according to claim 15 wherein the z-average diameter of the nano-disperse form of the dopant material is in the range of from 10 to 800 nm.

17. A water-soluble carrier liquid as claimed in claim 11, wherein the natural oils are selected from triglycerides, the non-vegetable oils are selected from silicone oils and paraffin oils, the waxes are selected from carnauba wax and candelilla wax, and the polymeric materials are selected from polyvinyl ethers, polyvinyl esters, polypropylene glycol and polyesters.

* * * * *